ус007981365B2

(12) United States Patent
Hart et al.

(10) Patent No.: US 7,981,365 B2
(45) Date of Patent: *Jul. 19, 2011

(54) ELECTROSPRAY COATING OF AEROSOLS FOR LABELING AND IDENTIFICATION

(75) Inventors: Matthew Hart, Alexandria, VA (US); Horn Bond Lin, Fairfax, VA (US); Jay Eversole, Woodbridge, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 536 days.

This patent is subject to a terminal disclaimer.

(21) Appl. No.: 11/229,431

(22) Filed: Sep. 15, 2005

(65) Prior Publication Data

US 2007/0059764 A1    Mar. 15, 2007

(51) Int. Cl.
*G01N 30/96*    (2006.01)
(52) U.S. Cl. .............. 422/88; 435/283.1; 435/288.7; 436/35; 436/149; 436/153; 436/172; 422/82.08; 422/83; 356/36; 356/37; 356/300; 356/318; 356/335; 250/281; 250/282; 250/283; 250/288; 250/299
(58) Field of Classification Search .......... 422/83, 422/86, 91–93, 98, 101–104; 435/286.2, 435/286.6, 286.7
See application file for complete search history.

(56) References Cited

U.S. PATENT DOCUMENTS

| | | | |
|---|---|---|---|
| 4,748,043 A * | 5/1988 | Seaver et al. ................. 427/482 |
| 5,076,097 A * | 12/1991 | Zarrin et al. ................. 73/61.72 |
| 5,208,651 A * | 5/1993 | Buican .......................... 356/451 |
| 5,306,412 A | 4/1994 | Whitehouse et al. |
| 5,366,858 A * | 11/1994 | Koizumi et al. ................. 435/5 |
| 5,523,566 A | 6/1996 | Fuerstenau et al. |
| 6,045,855 A | 4/2000 | Lindqvist |
| 6,087,183 A * | 7/2000 | Zaromb ........................ 436/178 |
| 6,297,499 B1 | 10/2001 | Fenn |
| 6,787,313 B2 * | 9/2004 | Morozov et al. ................. 435/6 |
| 2002/0012930 A1 * | 1/2002 | Rothberg et al. ................. 435/6 |
| 2003/0098421 A1 * | 5/2003 | Ho ........................... 250/458.1 |
| 2003/0199100 A1 * | 10/2003 | Wick ............................ 436/153 |
| 2003/0223063 A1 * | 12/2003 | Hill et al. ..................... 356/340 |

(Continued)

OTHER PUBLICATIONS

Gridin et al., "A renewable liquid droplet method for on-line pollution analysis by multi-photon ionization", Anal. Chem., 1997, vol. 69, pp. 2098-2102.*

(Continued)

*Primary Examiner* — N Yang
(74) *Attorney, Agent, or Firm* — Amy L. Reasing; Joseph T. Grunkemeyer

(57) ABSTRACT

A device having an air sampler, an electrospray apparatus, and a fluorescence excitation and detection system. The air sampler is capable of moving air suspected of containing a biological or chemical aerosol particle into a chamber. The electrospray apparatus is capable of spraying a charged solution into the chamber to coat the aerosol particles with a coating. The solution has a fluorescent-labeled biological or chemical marker capable of specific binding to the aerosol particle. The fluorescence system is capable of detecting fluorescence of the fluorescent label in the coating. A method of detecting the aerosol particle by: moving air suspected of containing the aerosol particle into a chamber; spraying the charged solution into the chamber with an electrospray apparatus, such that a coating of the solution is formed around the particle; exciting the fluorescent label; and detecting fluorescence of the fluorescent label.

18 Claims, 3 Drawing Sheets

U.S. PATENT DOCUMENTS

2004/0002166 A1* 1/2004 Wiederin .................... 436/181
2004/0075049 A1* 4/2004 Stowers et al. ............... 250/282
2004/0089156 A1   5/2004 Gartstein et al.
2005/0179893 A1* 8/2005 Hill ............................. 356/318
2005/0214168 A1* 9/2005 Lin et al. ....................... 422/83

OTHER PUBLICATIONS

Lermer et al., "High-efficiency molecular counting in solution: single-molecule detection in electrodynamically focused microdroplet streams", Anal. Chem., 1997, vol. 69, pp. 2115-2121.*

Ng et al., "Polymer microparticle arrays from electrodynamically focused microdroplet streams", Review of Scientific Instruments, 2000, vol. 71, pp. 2497-2499.*

Ramsey et al., "Generating electrospray from microchip devices using electroosmotic pumping", Anal. Chem., 1997, vol. 69, pp. 1174-1178.*

Sparkman, "A review of the 9th Sanibel conference on mass spectrometry quadrupole ion traps", J. Am. Soc. Mass Spectrom., 1997, vol. 8, pp. 569-572.*

Ogata et al., "Velocity Measurements of Electrostatically Sprayed Droplets by Means of Two Laser Pulses of Different Wavelenght" *J. Electrostatics*, 9, 223-234 (1981).

Wilhelm et al., "Electrospray evaporation and deposition" *Aerosol Sci.*, 34, 815-836 (2003).

Cloupeau et al., "Electrohydrodynamic Spraying Functioning Modes: A Critical Review" *J. Aerosol. Sci.*, 25(6), 1021-1036 (1994).

* cited by examiner

ELECTROSPRAY COATING OF AEROSOLS FOR LABELING AND IDENTIFICATION

BACKGROUND OF THE INVENTION

1. Field of the Invention

The invention is generally related to biological and chemical detection.

2. Description of the Related Art

Antibody conjugated fluorescent tagging (ACFT) has been used to locate and identify specific biological organisms based on antigen/antibody recognition and binding. If a sample contains the entity for which the antibodies are matched, they will bind to it. Antibodies, or other types of molecular binding entities such as molecular beacons or aptamers can be prepared with fluorescent markers, so when the sample mixture is rinsed the target species can be identified using optical methods. Through the use of self quenching or fluorescence resonant energy transfer (FRET), binding entities can be produced which do not fluoresce unless bound, creating a fluorescent switch to signal the presence of the targeted antigen. The use of these may allow for the labeling and subsequent identification of multiple types of aerosols at the same time. These types of biological markers, continue to be a high interest area of research and have been created for many types of biological particles such as proteins, viruses, and bacteria such as anthrax cells, spores, and related bacterial species used for biological threat simulants.

Current biological detection systems, which are based on the type of assay interrogations mentioned above, make the determination of the presence of particular aerosols by performing a complicated, multi-step process. The sampling, collection, and final assay procedures can consume a large amount of analyte and is generally time consuming.

SUMMARY OF THE INVENTION

The invention comprises a device comprising an air sampler, an electrospray apparatus, and a fluorescence excitation and detection system. The air sampler is capable of moving air suspected of containing a biological aerosol particle into a chamber. The electrospray apparatus is capable of spraying a charged solution into the chamber to coat the aerosol particles with a coating. The solution comprises a fluorescent-labeled biological or chemical marker capable of specific binding to the aerosol particle. The fluorescence system is capable of detecting fluorescence of the fluorescent label in the coating.

The invention further comprises a method of detecting a biological aerosol particle by: moving air suspected of containing the aerosol particle into a chamber; spraying a charged solution comprising a fluorescent-labeled biological or chemical marker capable of specific binding to the aerosol particle into the chamber with an electrospray apparatus, such that a coating of the solution is formed around the particle; exciting the fluorescent label; and detecting fluorescence of the fluorescent label.

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

The invention may be used to perform on-the-fly coating of specific aerosols with unique fluorescent markers so that they may be identified in real-time among a background of other particles. There are no other known methods to identify fine particles suspended in the atmosphere in a timely fashion. This method may allow the identification of single biological, or chemical particles within a few seconds of sampling.

One use of this technology may be the rapid detection of aerosolized chemical or biological threats in the air. Other uses would be for air quality control in confined and isolated areas such as submarines, airliners, and space vehicles. The small weight and footprint of a device using this technology may create the possibility for the detector to be carried in small remote controlled vehicles, on land or in air, into areas of suspected contamination or surveillance targets. Other general uses may include, but are not limited to, the monitoring of medical center air spaces and of specific pollens, fungal spores, and other seasonal allergens of interest. Only a small amount of consumables may be needed, which may potentially lend itself to long term operation requiring minimal maintenance.

There are three steps that may be done in order to accomplish this. 1) Initial charging of the aerosol. 2) Wetting of the aerosol using positively charged liquid drops containing the biological markers. 3) On-the-fly optical interrogation of the aerosols, on a particle by particle basis, for fluorescence signatures due to marker binding.

The device may optionally comprise a charger to charge the aerosol particles with the opposite charge as the charged solution (labeling solution or biomarker solution). This charging is done before the particles are coated. This is done because the wetting liquid will be positively charged such that electrical attraction can be used to facilitate the combining of the aerosols and the droplets for efficient wetting. Suitable chargers include, but are not limited to, a corona charger and a second electrospray apparatus.

Figure 2:
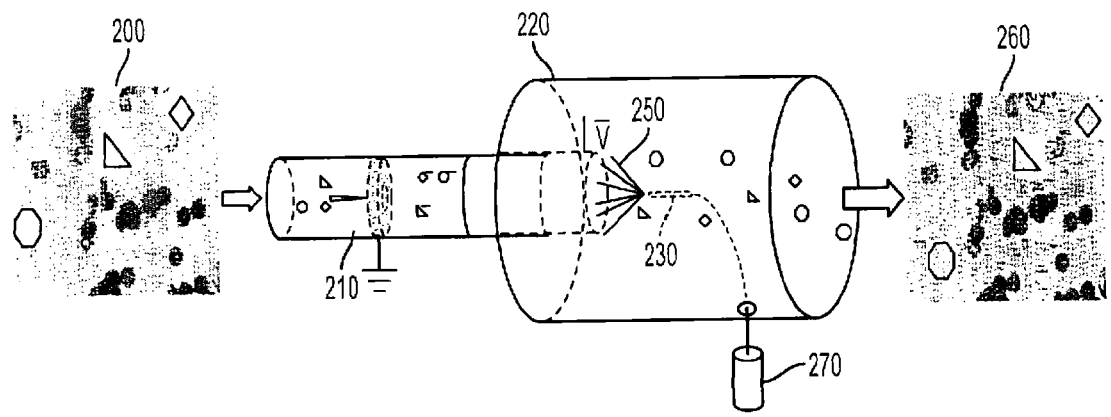
FIG. 2 schematically illustrates an aerosol coating system with particles flowing in from the left, being charged and then coated by liquid droplets created by an electrospray.
Figure 4:
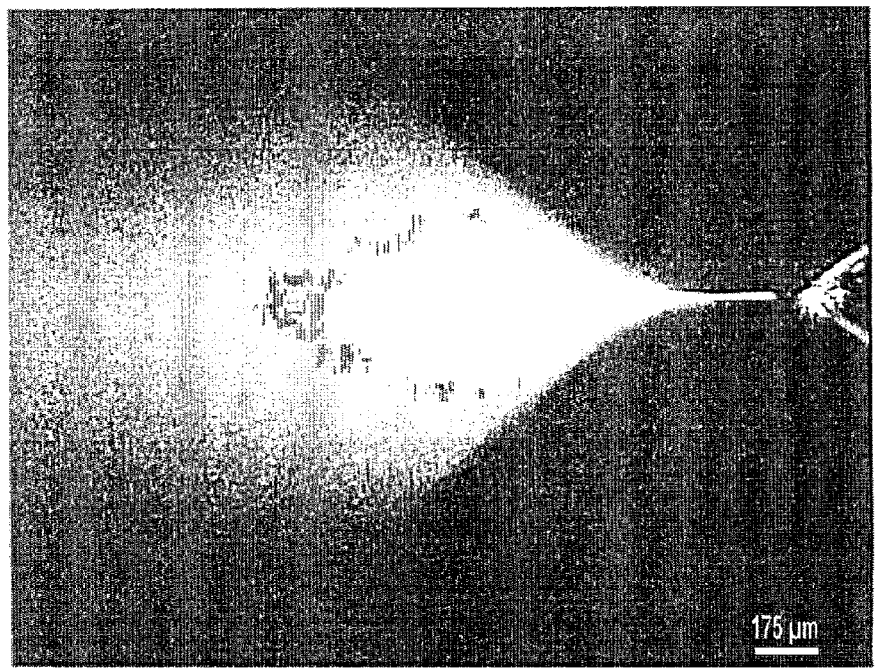
FIG. 4 shows a photograph of the droplet cone near the end of the nozzle of an electrospray.

The corona charger is a small inline device that uses an electrode needle that is in close proximity to a grounded plane. This is schematically illustrated in FIG. 4. When a high negative voltage potential is placed on the electrode 110, with respect to ground, the air near the tip of the electrode will become highly charged and ionized. This creates free floating negative charges flowing in the air stream along with the aerosols. The aerosols 130 collect the charges as they pass near the tip of the electrode of the corona charger, so that they will have a resultant negative charge 120 as they proceed into the coating section. FIG. 2 shows the input aerosol 200 from the ambient atmosphere, including the agents to be detected (shown as hollow). The aerosol passes through a corona charger 210, and into the coating section 220 containing an electrospray nozzle 230. The nozzle may point towards or away from the charger, or an any other direction that allows for coating the particles. The nozzle is fed by a solution of biomarkers 270. The nozzle produces positively charged droplets 250 containing the markers. The output 260 contains labeled aerosols (shown as solid) among a background of other aerosols.

A second electrospray apparatus may be used to coat the particles with another solution of opposite charge than that subsequently applied by the (first) electrospray apparatus.

Figure 1:
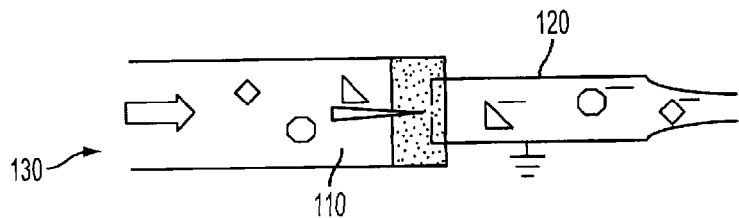
FIG. 1 schematically illustrates a corona charger.
Figure 3:
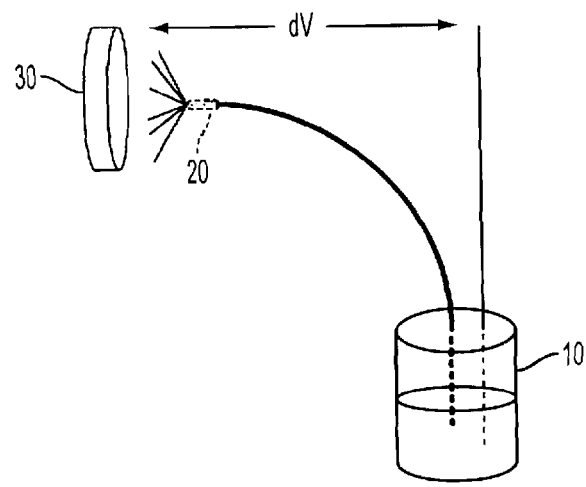
FIG. 3 schematically illustrates a basic electrospray setup.

The liquid droplets for the wetting of the aerosols are created using an electrospray. The droplets can contain the normally quenched (dark) biological markers specific for certain predetermined aerosols. The electrospray nozzle creates a cone of positively charged droplets which the negatively charged aerosols are forced to flow through. The electrospray is formed from the tip of a micron sized (such as 50-200 μm) capillary tube when a high voltage potential (such as 3-9 kV) is placed between the liquid and a grounding ring in front of the nozzle. Droplets are pulled from the tip of the nozzle due the high charge density on the surface of the liquid. The strong electrostatic forces on the surface of each droplet continuously break them into smaller and smaller volumes, until the surface charge density on the droplet is no longer great enough to overcome the surface tension of the liquid. Droplets the size of nanometers can be created by this process. Due to the strong electrostatic repulsion between the droplets themselves, the shape of the cone of droplets near the tip of the electrospray nozzle is independent of the shape of the grounding ring used to create the potential difference. It is in this zone where the droplets are biggest, in the order of microns, that the aerosols are forced through for wetting. FIG. 3 is an illustration of an example electrospray system, and FIG. 1 a close-up photograph of an electrospray in operation. FIG. 3 shows a solution of biomarkers 10, an electrospray nozzle 20, and a grounded ring 30. If a wetted aerosol is one of the particular ones that the biological markers have been made for then those specific markers will bind to the particle, and unquench, that is be allowed to fluoresce and be detected in the next stage.

The particular biomarker is chosen because it binds to a specific agent. For example, in the case of a bioweapon, it binds to a specific molecule or protein on the surface of a spore, vegetative cell, or to the protein itself in the case of protein toxins. When the quenched biomarker binds to the agent, the conformation of the binding mechanism changes so that the biomarker becomes fluorescent. The different binding events for the various particles can be differentiated by using differently colored fluorophores as emitters. Since the markers do not fluoresce unless bound to their intended binding site, multiple types of particles can be identified simultaneously using the same inhomogeneous solution of markers. In this way, the immunoassay step is effectively done in flight, on the surface of the aerosols. The binding mechanism of the biomarkers is general enough to work with aerosolized chemical agents (ricin, botulinum toxins, etc.) as well. Table 1 lists a number of (unquenched) example targets and publications in which an appropriate marker is disclosed. All referenced patent documents and publications are incorporated herein by reference.

TABLE 1

| Target: | Class: | Source: |
| --- | --- | --- |
| Anthrax protective antigen | Protein | Wilson, C. et al. (2004) PCT Publication No. WO2004085665 |
| Anthrax protective antigen | Protein | Air Force Research Laboratory |
| Cholera whole toxin | Protein | Bruno, J. G., et al. (2002) Biotechniques 32(1) 178-183 |
| Staphylococcal enterotoxin B | Protein | Bruno, J. G., et al. (2002) Biotechniques 32(1) 178-183 |
| HIV-1 nucleocapsid protein | Protein | Kim, S. J. et al. (2002) Biochem Biophys Res Commun 291(4) 925-931 |
| HIV-1 Tat | Protein | Yamamoto, R. et al. (2000) Genes Cells 5(5) 389-396 |
| Ricin | Protein | Hesselberth, et al. (2000) J Biol Chem 275(7) 4937-4942 |
| Shiga Toxin | Protein | Air Force Research Laboratory |
| Hepatitis C NS3 | Protein | Fukuda, et al. (2000) Eur J Biochem 267(12) 3685-3694 |
| Anthrax spores | Spore | Bruno, J. G. et al. (1999) Biosens Bioelectron 14(5) 457-464 |
| African trypanosomes | Protozoa | Homann, et al. (1999) Nucleic Acids Res 27(9) 2006-2014 |
| Glioblastoma-derived U251 | Cancer cells | Daniels, D. A. et al. (2003) PNAS USA 100(26) 15416-15421 |
| Vitamin B12 | Small molecule | Sussman, D. et al. (2000) Structure Fold Des 8(7) 719-27 |
| Flavin Adenine Dinucleotide | Small molecule | Roychowdhury-Saha M, et al. (2002) Biochemistry 41(8) 2492-2499 |
| Tetracycline | Small molecule | Berens, C. et al. (2001) Bioorg Med Chem 10 2549-2556 |
| 16S Ribosomal RNA | Nucleic acid | Tok, J. B. et al. (2000) Nucleic Acids Res 28(15) 2902-2910 |
| Transcription termination factor rho | Nucleic acid | Schneider, D. et al. (1993) FASEB J 7(1) 201-207 |
| HIV-1 TAR RNA element | Nucleic acid | Collin, D. et al. (2000) Nucleic Acids Res 28(17) 3386-3391 |
| Tryptophan/agarose | Carbohydrate | Famulok, M (1992) JAm Chem Soc 114(10) 3990-3991 |

Different types of fluorescent labels may be used. One type does not fluoresce unless the biological marker is bound to the aerosol particle. Another type fluoresces at a first wavelength when the biological marker is not bound to the aerosol particle and at a second wavelength when the biological marker is bound to the aerosol particle. In one embodiment, the solution comprises more than one different fluorescent-labeled biological or chemical marker, each marker being capable of specific binding to a different aerosol particle.

Figure 5:
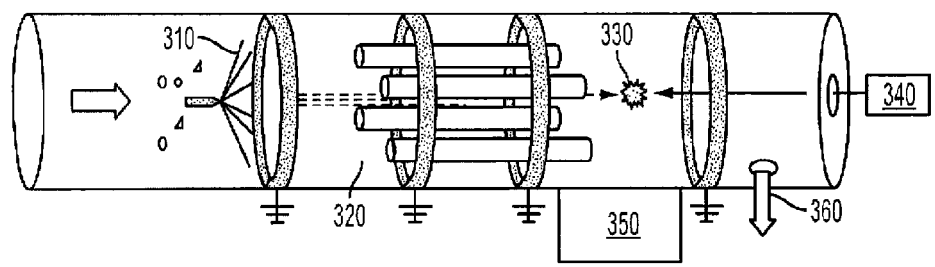
FIG. 5 schematically illustrates the flow stream showing the various sections, from left to right, the electrospray, electrodynamic linear quadrupole (ELQ), and optical interrogation.

The fluorescence excitation and detection system may comprise a laser oriented to illuminate the coated aerosol particles with laser energy and a photomultiplier tube oriented to detect the fluorescence emitted by the fluorescent label. Further optional components of the fluorescence system include, but are not limited to, a detector capable of detecting laser energy scattered from the coated particles and an electrodynamic linear quadrupole (ELQ) capable of confining the coated particles within a cylindrical region There are already systems available that illuminate single particles on-the-fly and look for fluorescent emission for use in an optical interrogation stage. These devices are typically used as the trigger mechanism for current aerosol detectors. The aerosols are entrained through a small nozzle and intercepted by a laser pulse, usually of ultraviolet wavelength, just as they exit. In the system described here, the particles may in general have a residual positive charge due to the electrospray process. An ELQ may be used to focus the aerosols along the axis of flow so that they will be concentrated at a point at which they can be interrogated by a laser inducing fluorescence system as described above. This may increase the fraction of particles that flow through to the detection area, as opposed to colliding with and sticking to the interior walls of the device. FIG. 5 shows the aerosol passing through the coating section 310 and ELQ 320. The fluorescently labeled aerosol 330 is then illuminated by a laser 340. A fluorescent light detector 350 detects the fluorescence. Arrow 360 indicates air flow leaving the tube.

Typical air flow rates through the system may be from less than 1 L/min to greater than 10 L/min, which can result in travel times of just a few seconds, from the time the aerosols are initially brought into the system and charged, to when they are optically interrogated for labeled fluorescence. This time scale is extremely rapid as compared to current systems which can take several minutes to make a determination. The flow rate of the electrospray liquid may be less than 10 milliliters per day, and may be constant. This is much less than what current systems use, which can amount to liters per day, depending on how many times that system is triggered for sample collection, and the comparatively large volume assay analysis.

The system naturally follows a cylindrical geometry and can require a length of less than 20 inches, as has been demonstrated with the first prototype. Additionally, this technology can utilize red or near infrared laser wavelengths to excite fluorescent labels of longer wavelengths, which are commonly available. Such labels would keep the wavelength of the fluorescent labels above that of the intrinsic biological fluorescence of aerosols which would be a source of background noise, and which drops off considerably above 600 nm. Also, laser diode powers are commonly much higher in the red or near infrared which is convenient for more efficient optical interrogation.

Having described the invention, the following example is given to illustrate specific applications of the invention. This specific example is not intended to limit the scope of the invention described in this application.

EXAMPLE

Figure 6:
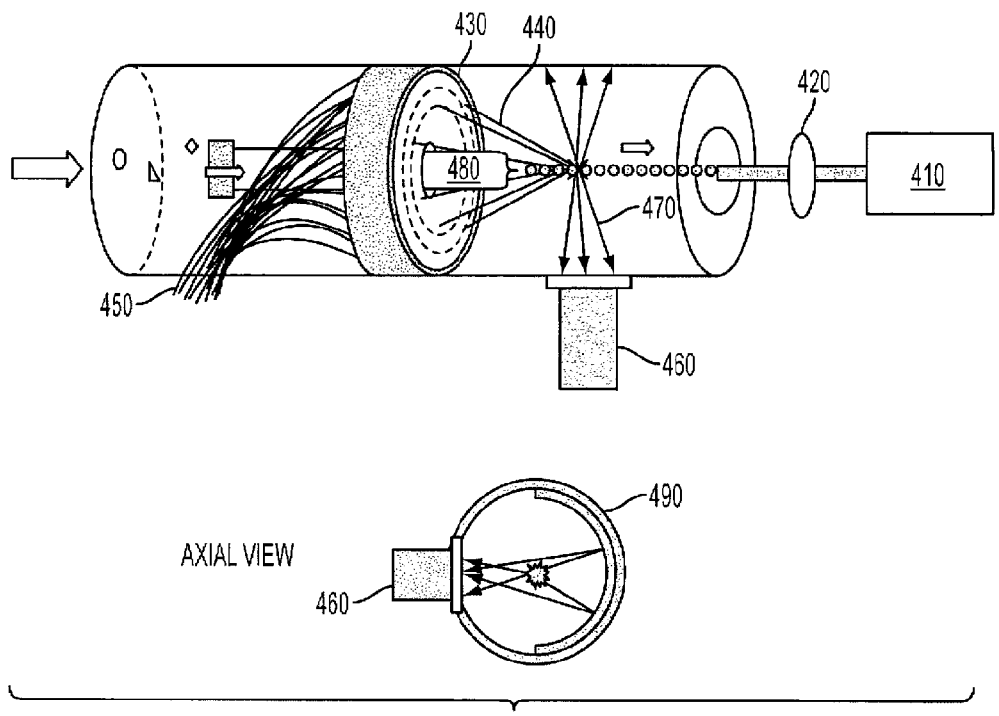
FIG. 6 schematically illustrates a simple laser interrogation setup used to detect single aerosols on-the-fly.

A prototype was built to demonstrate the basic coating principle based on the electrospray technique. A diagram of the laser interrogation section setup is shown in FIG. 6. The prototype consisted of a 14 inch long, clear plastic tube with an inside diameter of 1.5 inches. The electrospray area (not shown) made up the left section of the tube, and a simple laser interrogation stage (LIS) was in the right half of the tube. Air flow was achieved, from left to right, with the use of a pump connected on the right side of the tube. A green laser beam 410 was directed through a focusing optic 420 along the axis of the tube, from right to left, and illuminated the electrospray area inside the tube and an aperture outside of the tube near the right end, where the light passed into the LIS through a window. Aerosols were sucked into the tube from the left end, passed through the electrospray portion, through an aerodynamic nozzle 480 and then into the LIS. With flow rates of one to 10 liters per minute, the travel time for the aerosols through the system was less than five seconds.

A fiber array 430 collected the laser light which was directly scattered 440 from the aerosols (elastic scatter) into a fiber bundle 450 and then funneled into a photomultiplier tube (PMT). This signal was used to detect the presence of an aerosol whether it had been fluorescently labeled or not. The side mounted PMT 460 was used to detect the presence of a fluorescent signal 470 from a labeled aerosol. A mirrored back surface 490 directed more light towards the PMT.

Figure 7:
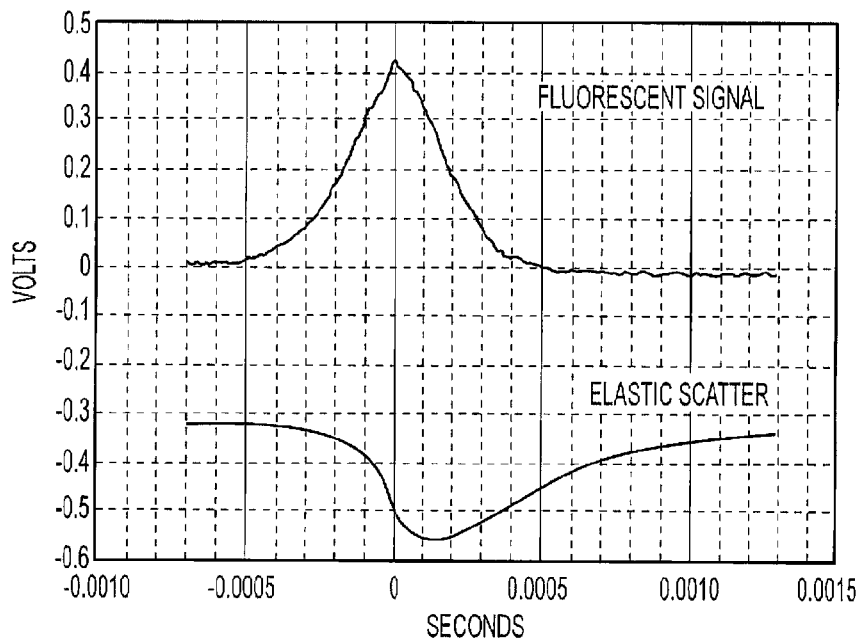
FIG. 7 shows typical signals from single, fluorescently doped, 1 micron microspheres gathered from the PMTs using the simple laser interrogation setup.

FIG. 7 shows the average over many traces from the detection scheme depicted in FIG. 6. The data is from 1 micron diameter fluorescently doped microspheres obtained from Molecular Probes, Incorporated.

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed is:

1. A device comprising:
   an air sampler capable of moving air suspected of containing a biological or chemical aerosol particle into a chamber;
   an electrospray apparatus capable of spraying a charged solution into the chamber to coat the aerosol particles with a coating;
      wherein the solution comprises a fluorescent-labeled biological or chemical marker capable of specific binding to the aerosol particle; and
   a fluorescence excitation and detection system capable of detecting fluorescence of the fluorescent label in the coating of the coated aerosol particles.

2. The device of claim 1, further comprising:
   a charger capable of charging the aerosol particles with a charge opposite to the charged solution, before the aerosol particles are coated.

3. The device of claim 2, wherein the charger is selected from the group consisting of a corona charger and a second electrospray apparatus.

4. The device of claim 1, wherein the fluorescence excitation and detection system comprises:
   a laser oriented to illuminate the coated aerosol particles with laser energy; and
   a photomultiplier tube oriented to detect the fluorescence emitted by the fluorescent label.

5. The device of claim 4, wherein the fluorescence excitation and detection system further comprises:
   a detector capable of detecting laser energy scattered from the coated aerosol particles.

6. The device of claim 4, further comprising:
   an electrodynamic linear quadrupole capable of confining the coated aerosol particles within a cylindrical region.

7. A method of detecting a biological or chemical aerosol particle comprising:
   moving air suspected of containing the aerosol particle into a chamber;
   spraying a charged solution comprising a fluorescent-labeled biological or chemical marker capable of specific binding to the aerosol particle into the chamber with an electrospray apparatus, such that a coating of the solution is formed around the particle;
   exciting the fluorescent label in the coating of the coated aerosol particles; and
   detecting fluorescence of the fluorescent label in the coating of the coated aerosol particles.

8. The method of claim 7, further comprising:
   charging the aerosol particles with a charge opposite to the charged solution, before the aerosol particles are coated.

9. The method of claim 8, wherein the charging is selected from the group consisting of a corona charger and a second electrospray apparatus.

10. The method of claim 7, wherein exciting the fluorescent label is performed by illuminating the coated aerosol particles with laser energy.

11. The method of claim 7, wherein detecting the fluorescence is performed a photomultiplier tube oriented to detect the fluorescence emitted by the fluorescent label.

12. The method of claim 10, further comprising:
    detecting laser energy scattered from the coated aerosol particles.

13. The method of claim 10, further comprising:
    confining the coated aerosol particles within a cylindrical region.

14. The method of claim 7;
    wherein the fluorescent label does not fluoresce unless the biological marker is bound to the aerosol particle.

15. The method of claim 7, wherein the fluorescent label fluoresces at a first wavelength when the biological marker is not bound to the aerosol particle and at a second wavelength when the biological marker is bound to the aerosol particle.

16. The method of claim 7, wherein the solution comprises more than one different fluorescent-labeled biological or chemical marker, each marker being capable of specific binding to a different aerosol particle.

17. The device of claim 1, wherein the electrospray apparatus comprises a capillary tube and a grounding ring.

18. The method of claim 7, wherein the electrospray apparatus comprises a capillary tube and a grounding ring.

\* \* \* \* \*